United States Patent
Polymeropoulos

(10) Patent No.: US 11,071,728 B2
(45) Date of Patent: Jul. 27, 2021

(54) TREATMENT OF SCHIZOPHRENIA

(71) Applicant: Vanda Pharmaceuticals Inc., Washington, DC (US)

(72) Inventor: Mihael H. Polymeropoulos, Potomac, MD (US)

(73) Assignee: Vanda Pharmaceuticals Inc., Washington, DC (US)

( * ) Notice: Subject to any disclaimer, the term of this patent is extended or adjusted under 35 U.S.C. 154(b) by 164 days.

(21) Appl. No.: 15/375,727

(22) Filed: Dec. 12, 2016

(65) Prior Publication Data

US 2017/0165250 A1 Jun. 15, 2017

Related U.S. Application Data

(60) Provisional application No. 62/266,541, filed on Dec. 11, 2015.

(51) Int. Cl.
*A61K 31/454* (2006.01)
*A61K 9/00* (2006.01)

(52) U.S. Cl.
CPC .......... *A61K 31/454* (2013.01); *A61K 9/0024* (2013.01)

(58) Field of Classification Search
CPC ........................... A61K 31/454; A61K 9/0053
See application file for complete search history.

(56) References Cited

U.S. PATENT DOCUMENTS

| 8,227,488 B2 | 7/2012 | Wiekhusen et al. |
| 8,815,293 B2 | 8/2014 | Ahlheim et al. |

OTHER PUBLICATIONS

Scott, CNS Drugs, 2009, 23(10):867-880.*
Caccia et al, Drug Design, Development and Therapy, 2010:4, 33-48.*
FANAPT, pp. 1-23 (Year: 2009).*
Montes et al (Drug Forecast, Nov. 2009, vol. 34, No. 11, pp. 606-613) (Year: 2009).*
Muzyk et al (J Neuropsychiatry Clin Neurosci, 24:2, Spring 2012) (Year: 2012).*

* cited by examiner

*Primary Examiner* — Sudhakar Katakam
(74) *Attorney, Agent, or Firm* — Hoffman Warnick LLC

(57) ABSTRACT

Aspects of the invention relate generally to the treatment of schizophrenia and to monitoring for specific adverse reactions.

3 Claims, No Drawings

TREATMENT OF SCHIZOPHRENIA

CROSS-REFERENCE TO RELATED APPLICATIONS

This application claims the benefit of U.S. Provisional Patent Application Ser. No. 62/266,541, filed 11 Dec. 2015, which is hereby incorporated herein as though fully set forth.

BACKGROUND

This invention is in the field of treatment of schizophrenia and other central nervous system disorders with the atypical antipsychotic, iloperidone.

Iloperidone, a mixed D2/5HT2 antagonist, was approved by the US Food and Drug Administration ("FDA") for the treatment of schizophrenia in 2009 based on short-term acute efficacy studies. It is marketed with the brandname, FANAPT®.

The prescribing information, sometimes referred to as the label, approved as of the priority date of this application contains the following with respect to hypersensitivity to iloperidone:

Contraindications

Known hypersensitivity to FANAPT or to any components in the formulation. (4) and 4 Contraindications FANAPT is contraindicated in individuals with a known hypersensitivity reaction to the product. Reactions have included pruritus and urticaria.

DETAILED DESCRIPTION OF THE INVENTION

This invention comprises the discovery through post-marketing experience that treatment of patients with iloperidone has been associated with specific adverse reactions. These include anaphylaxis, angioedema, throat tightness, oropharyngeal swelling, swelling of the face, lip, mouth, and tongue; urticaria, rash, and pruritus.

Thus, an aspect of this invention comprises monitoring patients on iloperidone specifically for these reactions. If one or more of these reactions occur, iloperidone can be discontinued or the dose can be adjusted downward. In the case of discontinuation, the patient can be switched to a different medication, e.g., a different atypical antipsychotic or other antipsychotic. It may also be appropriate to treat the reaction, e.g., with epinephrine or steroid therapy.

Without limiting this invention to a particular mechanism of action, the enumerated reactions may be hypersensitivity reactions. An aspect of this invention therefore comprises amending the contraindications section and/or the adverse events section of the iloperidone package insert, i.e., prescribing information, to read more or less as follows:

4 Contraindications
FANAPT is contraindicated in individuals with a known hypersensitivity reaction to the product. Anaphylaxis, angioedema, and other hypersensitivity reactions have been reported [see Adverse Reactions (6.2)]
and
6.2 Postmarketing Experience
The following adverse reactions have been identified during post-approval use of FANAPT-: retrograde ejaculation and hypersensitivity reactions (including anaphylaxis, angioedema, throat tightness, oropharyngeal swelling, swelling of the face, lip, mouth, and/or tongue; urticaria, rash, and pruritus). Because these reactions were reported voluntarily from a population of uncertain size, it is not possible to reliably estimate their frequency or establish a causal relationship to drug exposure.

Illustrative embodiments of this invention include the following.

A method of treating a patient with iloperidone, said method comprising:
monitoring the patient specifically for one or more of the following hypersensitivity reactions while the patient is being treated with iloperidone: anaphylaxis, angioedema, throat tightness, oropharyngeal swelling, swelling of the face, lip, mouth, and tongue, and rash; and
if one or more of the recited hypersensitivity reactions occurs, then discontinuing treatment with iloperidone or reducing the dose of iloperidone.

A method of treating a patient with iloperidone, said method comprising:
administering iloperidone to the patient at a dose of 12 to 24 mg/d by oral delivery once daily or by intramuscular or subcutaneous injection of a depot form of iloperidone once monthly;
monitoring the patient specifically for one or more of the following hypersensitivity reactions while the patient is being treated with iloperidone: anaphylaxis, angioedema, throat tightness, oropharyngeal swelling, swelling of the face, lip, mouth, and/or tongue; and rash; and
if one or more of the recited hypersensitivity reactions occurs, then discontinuing treatment with iloperidone or reducing the dose of iloperidone.

A method of treating a patient with iloperidone, said method comprising:
administering iloperidone to the patient at a dose of 12 to 24 mg/d, e.g., 16 to 24 mg/d, by oral delivery once daily or by intramuscular or subcutaneous injection of a depot form of iloperidone once monthly;
monitoring the patient specifically for one or more of the following hypersensitivity reactions while the patient is being treated with iloperidone: anaphylaxis, angioedema, throat tightness, oropharyngeal swelling, swelling of the face, lip, mouth, and/or tongue; and rash; and
if one or more of the recited hypersensitivity reactions occurs, then reducing the dose of iloperidone to 8 to 16 mg/d, e.g., 12 to 16 mg/d.

A method of reducing the frequency or severity of adverse events associated with iloperidone administration, said method comprising:
monitoring the patient specifically for one or more of the following hypersensitivity reactions while the patient is being treated with iloperidone: anaphylaxis, angioedema, throat tightness, oropharyngeal swelling, swelling of the face, lip, mouth, and/or tongue; and rash; and
if one or more of the recited hypersensitivity reactions occurs, then discontinuing treatment with iloperidone or reducing the dose of iloperidone.

A method of treating a patient with iloperidone and to improve the safety of such therapy, said method comprising:
informing the patient or the patient's guardian or healthcare provider that anaphylaxis, angioedema, throat tightness, oropharyngeal swelling, swelling of the face, lip, mouth, and tongue, and rash are possible side effects of iloperidone therapy and that the patient should seek prompt medical attention if such symptoms are experienced by the patient.

Additional illustrative embodiments include any one or more of the above embodiments wherein the iloperidone treatment is restarted following a discontinuation period or wherein the dose is increased following a low reduced dose period.

The above embodiments wherein the monitoring comprises instructing the patient, the patient's guardian, or the patient's healthcare provider, e.g., medical doctor, that the following adverse reactions have been identified during post-approval use of iloperidone: hypersensitivity reactions (including anaphylaxis, angioedema, throat tightness, oropharyngeal swelling, swelling of the face, lip, mouth, and/or tongue, urticaria, rash, and pruritus).

The above embodiments wherein the monitoring comprises monitoring for occurrence of swollen tongue and/or swollen lip.

The above embodiments wherein the level of monitoring is heightened meaning that very early and/or relatively minor symptoms, which under normal circumstances would not be a cause for deviation from treatment, cause the discontinuation of iloperidone treatment or the reduction of iloperidone dose, usually couple with earlier follow up examination.

Among the enumerated reactions, rash was the most common followed by swollen tongue and swollen lip.

Informing patients or their guardians or healthcare providers can be accomplished, e.g.: verbally, by video, textual, or audio instructions, or by including such information in the product label, i.e., in the prescribing information.

This invention may also comprise physicians instructing patients to monitor themselves for these side effects and to report back to the physician and/or to self-discontinue treatment with iloperidone in case of experiencing one or more of these side effects pending an examination and consult with the physician.

This invention can also comprise requiring pharmacies not to dispense iloperidone unless and until a pharmacist or other pharmaceutical dispenser has cautioned the patient about these adverse events and has advised the patient to contact his or her physician or other healthcare provider immediately if one or more of the adverse events occurs.

Depot forms of iloperidone are disclosed, e.g., in U.S. Pat. Nos. 8,815,293 and 8,227,488.

The present invention can be carried out in conjunction with other treatment approaches, e.g., in combination with a second or multiple other active pharmaceutical agents, including but not limited to agents that affect insomnia, sleep-wake patterns, vigilance, depression, or psychotic episodes.

While this invention has been described in conjunction with the specific embodiments outlined above, it is evident that many alternatives, modifications and variations will be apparent to those skilled in the art or are otherwise intended to be embraced. Accordingly, the embodiments of the invention as set forth above are intended to be illustrative, not limiting. Various changes may be made without departing from the spirit and scope of the invention as defined in the following claims. All patents, patent application, scientific articles and other published documents cited herein are hereby incorporated in their entirety for the substance of their disclosures.

The invention claimed is:

1. A method of treating a patient with iloperidone who has previously exhibited one or more hypersensitivity reaction when treated with a first dose of iloperidone that is between 12 mg/day and 24 mg/day, the method comprising:
   administering to the patient a second dose of iloperidone that is between 8 mg/day and 16 mg/day and less than the first dose of iloperidone,
   wherein the hypersensitivity reaction includes one or more of anaphylaxis; angioedema; throat tightness; oropharyngeal swelling; or swelling of the face, lip, mouth, or tongue.

2. The method of claim 1, wherein administering includes orally administering the second dose of iloperidone.

3. The method of claim 1, wherein administering to the patient the second dose of iloperidone occurs following a discontinuation period.

* * * * *